ered Patent [19]

Fuhrmann

[11] 4,063,446
[45] Dec. 20, 1977

[54] METHOD OF AND APPARATUS FOR AUTOMATICALLY DETECTING TRACES OF ORGANIC SOLVENT VAPORS IN AIR

[76] Inventor: Hans Fuhrmann, Pannsweg 2, 2000 Hamburg 62, Germany

[21] Appl. No.: 734,614

[22] Filed: Oct. 21, 1976

Related U.S. Application Data

[63] Continuation of Ser. No. 573,421, May 1, 1975, abandoned.

[30] Foreign Application Priority Data

May 8, 1974 Germany ............................. 2422270
Dec. 16, 1974 Germany ............................. 2459343

[51] Int. Cl.² .............................................. G01N 31/06
[52] U.S. Cl. .......................................... 73/1 G; 73/23; 261/107
[58] Field of Search ................... 73/23, 1 G; 122/366, 122/5; 159/1 W, 16 R, 16 A, DIG. 27, DIG. 28; 261/104, 107

[56] References Cited

U.S. PATENT DOCUMENTS

| | | | |
|---|---|---|---|
| 2,965,842 | 12/1960 | Jacobson | 73/23 |
| 3,309,021 | 3/1967 | Powers | 159/1 W |
| 3,611,790 | 10/1971 | Brouwer et al. | 73/1 G |
| 3,888,112 | 6/1975 | De Leeuw et al. | 73/1 G |
| 3,954,920 | 5/1973 | Heath | 261/104 |

*Primary Examiner*—Richard C. Queisser
*Assistant Examiner*—Stephen A. Kreitman
*Attorney, Agent, or Firm*—Toren, McGeady and Stanger

[57] ABSTRACT

Method and apparatus for detecting minute traces of a gas in the PPB range ($\mu g.m^{-3}$) by pumping a gas mixture through a non-specific gas detector measuring cell and displaying and/or recording the signals generated by the measuring cell. For zero point control, the looked-for constituent in the gas mixture is eliminated therefrom by passing the gas mixture through an activated charcoal filter in which the looked-for constituent is retained, and pumping the cleaned gas mixture through the gas detector. For calibration, a liquid of a type corresponding to the looked-for constituent is evaporated in an evaporator, and a gas mixture of a predetermined concentration is pumped through the measuring cell. For quick calibration, the liquid is continuously evaporated in the evaporator, and during measuring or zero controls this evaporated gas is vented to the atmosphere. Flow rates are adjusted by means of capillary systems. Measuring, zero control and calibration cycles may be initiated automatically through a program controller.

5 Claims, 9 Drawing Figures

METHOD OF AND APPARATUS FOR AUTOMATICALLY DETECTING TRACES OF ORGANIC SOLVENT VAPORS IN AIR

This is a Continuation of application Ser. No. 573,421 filed May 1, 1975, now abandoned.

The present invention relates to a method of and an apparatus for automatically detecting traces of organic solvent vapors in air, in using a measuring cell in the form of a non-specific gas detector, particularly a gas detector semiconductor element, and performing comparative measurements of a test gas sample containing the measured component and a reference gas sample containing the measured component.

When it is desired to control or monitor the atmosphere in working spaces or the air exhausted from processing plants with respect to entrapped gases or vapors of organic compounds such as organic solvents, generally air samples are collected, and these samples are then analytically evaluated. The collecting of the samples and the transfer of the same into suitable apparatus for determining concentrations such as gas chromatographs or IR spectrophotometers is quite cumbersome and time consuming. Moreover, the capital expenditure and the operating costs of suitable apparatus are rather high. For the operation, skilled personnel is required. Simpler physical measurements such as methods based on the principles of thermal conductivity or heat absorption are not sufficiently sensitive in the ranges of interest of maximum admissible working place concentrations. Furthermore, these simpler methods are non-specific.

There are already known various types of semiconductor gas detectors wherein the gas sensitive element consists of a tin, zinc or Fe-III oxide. Gas detectors are more sensitive by several orders of magnitude but likewise non-specific and furthermore highly unstable.

There have already been proposed arrangements for generating gaseous mixtures in the PPB range ($\mu$g.m$^{-3}$). These systems, however, include diffusion diaphragms in combination with a supply of gases which are chemically bonded to predetermined liquids. Systems of this type may be employed for detecting gaeous $SO_2$ traces. The reservoir contains predominantly a highly concentrated chemically bonded gas which may be adjusted to smaller diffusion rates by suitable mechanical devices such as diaphragms, and then admixed to a carrier gas stream.

It is now an object of the present invention to provide a novel and improved method of automatically detecting traces of organic solvent vapors in air, and a respective apparatus therefor.

It is another object of the present invention to provide method and apparatus of the above type wherein may be employed semiconductor gas detectors as a measuring cell for quantitative measurements of gas traces and wherein may be obtained very precise results even for minute traces of the detected measured component.

In accordance with the present invention there is now proposed a method of the type as stated in the introduction, and this method is characterized by the steps of supplying to the gas detector measuring cell alternatively, for zero, calibration and measuring cycles, the test gas from which the measured component has been eliminated, test gas containing the measured component, and a mixture of solvent vapor of a type corresponding to the measured gas component with test gas from which the measured component has been eliminated, evaporating a liquid solvent of a type corresponding to the measured gas component to provide the mixture of solvent vapor and test gas from which the measured gas component has been eliminated, for calibration, maintaining constant the solvent/gas equilibrium when test gas from which the measured gas component has been eliminated flows in a pressureless stream through the evaporator space, this constant equilibrium being maintained independently of the level and the quantity of solvent within the evaporator space, admixing the test gas from which the measured gas component has been eliminated with the solvent vapor in a similar cycle for calibration, continuously repeating, at variable intervals, the zero control and calibration operations, and comparing electrically, in a measuring bridge, the measured values obtained in the measuring cell with an actual, stored reference value.

In a particular embodiment of the inventive method the stability and the response speed of the calibration operation may be increased by introducing the test gas sample, in direct flow, into the measuring device, passing the zero reference sample through a first activated charcoal filter and introducing the zero reference sample, similarly, in a direct flow into the measuring device, feeding the gas flow during the calibration cycle in a closed circuit path through a second activated charcoal filter and through capillary system, separating the measured gas component from the calibration gas exiting from the measuring cell by means of the second activated charcoal filter, diluting the concentrated measured gas component with gas supplied from the clibration gas generator through capillary tubes, adjusting the diluted measured gas component to a constant calibration value and then reintroducing the adjusted gas component into the measuring cell.

The furthermore proposed apparatus for automatically detecting traces of organic solvent vapors in air, in using a measuring cell in the form of a non-specific gas detector, particularly a gas detector semiconductor element, and performing comparative measurements of a test gas sample containing the measured component and a reference gas sample containing the measured component comprises a feed line for test gas, the feed line connected to a gas pump via a flow controller and a gas detector measuring cell, a control valve connected in the feed line, a first branch line connected to the feed line at two points respectively located downstream and upstream of the control valve, the first branch line including, in series connection, a second control valve and an activated charcoal filter, a second branch line connected to the feed line at a point upstream of the activated charcoal filter and downstream of the measuring cell, the second branch line connected to an outlet connector of a calibration unit through a third control valve and a capillary tube, the latter being connected between the third control valve and the outlet connector whereby the first, second and third control valves consist of solenoid operated valves connected to program control means.

In accordance with a specific embodiment of the present invention the apparatus comprises a feed line for test gas, the feed line connected to a gas pump via a flow controller and a gas detector measuring cell, a control valve connected in the feed line, a first branch line connected to the feed line at two points respectively located downstream and upstream of the control valve, the first branch line including, in series connection, a second control valve and an activated charcoal filter, a second branch line connected to the feed line at a point upstream of the activated charcoal filter and downstream of the measuring cell, the second branch line connected to an outlet connector of a calibration unit through a third control valve and a capillary tube, the latter being connected between the third control valve and the outlet connector whereby the first, second and third control valves consist of solenoid operated valves connected to program control means, the calibration unit including a washing-bottle type heat insulated receptacle into which extends an inlet line adapted to supply test gas from which the measured gas component has been eliminated into the receptacle, the inlet line having an an end orifice disposed above the level of fluid in the clibration receptacle, an outlet line connected to a dome-shaped top header portion of the receptacle, the outlet line adapted to discharge a solvent vapor/test gas mixture from the calibration unit, and large surface evaporator means disposed within the interior cavity of the receptacle.

In accordance with a still further embodiment the apparatus of the present invention comprises a feed line for test gas, the feed line connected to a gas pump via a flow controller and a gas detector measuring cell, a control valve connected in the feed line, a first branch line connected to the feed line at two points respectively located downstream and upstream of the control valve, the first branch line including, in series connection, a second control valve and an activated charcoal filter, a second branch line connected to the feed line at a point upstream of the activated charcoal filter and downstream of the measuring cell, the second branch line connected to an outlet connector of a calibration unit through a third control valve and a capillary tube, the latter be-ing connected between the third control valve and the outlet connector whereby the first, second and third control valves consist of solenoid operated valves connected to program control means, the calibration unit including a washing-bottle type heat insulated receptacle into which extends an inlet line adapted to supply test gas from which the measured component has been eliminated into the receptacle, the inlet line having an end orifice disposed above the level of fluid in the calibration receptacle, an outlet line connected to a dome-shaped top header portion of the receptacle, the outlet line adapted to discharge a solvent vapor/test gas mixture from the calibration unit, large surface evaporator means disposed within the internal cavity of the receptacle, the measuring cell connected to a measuring system, the measuring system including a fixed resistor and a pair of resistors, the pair of resistors being connected in a Wheatstone bridge circuit including a measuring potentiometer coupled to a first servo motor, and a zero potentiometer coupled to a second servo motor.

For maintaining the gas or respectively the vapor concentration in the calibration unit, a third branch line may be connected at one end to the second branch line at a point upstream of the capillary tube in the second branch line connected to the calibration unit, the other end of the third branch line may be connected to the feed line at a point intermediate the measuring cell and the flow controller, and the third branch line may include an auxiliary capillary tube. With this third branch line, a small partial stream is continuously withdrawn from the calibration unit through the capillary tube which is connected upstream thereof. This provides the advantage that upon opening of the valve in the feed line the required calibration gas concentration is immediately available and there is obtained a fast response of the calibration value.

The calibration unit consists of a washing-bottle type heat insulated receptacle. An inlet line adapted to supply test gas from which the measured gas component has been eliminated extends into the receptacle so that the end orifice of the inlet line is disposed above the level of fluid within the calibration receptacle. The receptacle comprises a dome-shaped top header portion to which is connected an outlet line adapted to discharge a solvent vapor/test gas mixture from the calibration unit. Within the internal cavity of the receptacle is disposed a large surface evaporator which may either comprise at least one filter paper cartridge in which filter paper is folded in the shape of a cylindrical sleeve of a star-shaped crosssectional configuration or a plurality of coaxially and concentrically arranged bodies made of a ceramic material. For maintaining a constant temperature, the receptacle of the calibration unit is preferably enclosed in an outer jacket of a heat insulating material, and this outer jacket is provided with heating means such as electrical heating elements.

In a particular embodiment of the inventive apparatus the test gas rate response speed may be increased by the expedients that the apparatus comprises a feed line for test gas, in the feed line being mounted in series a first shutoff valve, a rotameter, a measuring cell, a second shutoff valve, a first capillary tube, a second capillary tube, a diaphragm pump and a third capillary tube, a first branch line is connected in parallel to the feed line and c/onnected at one end to the feed line at a point between the measuring cell and the second shutoff valve, and at the other end to a point between the second shutoff valve and the first capillary tube, the first branch line including a first activated charcoal filter and a third shutoff valve, a second branch line connecting a calibration unit via a fourth capillary tube to the feed line at a point between the first and second capillary tubes, a third branch line connecting a second activated charcoal filter via fourth and fifth shutoff valves to the feed line at a point between the first shutoff valve and the rotameter, a fourth branch line connecting the third branch line at a point between the fourth and fifth shutoff valves to the feed line at a point between the diaphragm pump and the third capillary tube, the fourth branch line including a sixth shutoff valve.

The invention will be discribed more in detail with reference to the appended drawing wherein FIG. 1 is a schematical illustration of a first embodiment of an apparatus for automatically detecting traces of organic solvent vapors in air in accordance with the present invention;

Figure 1:
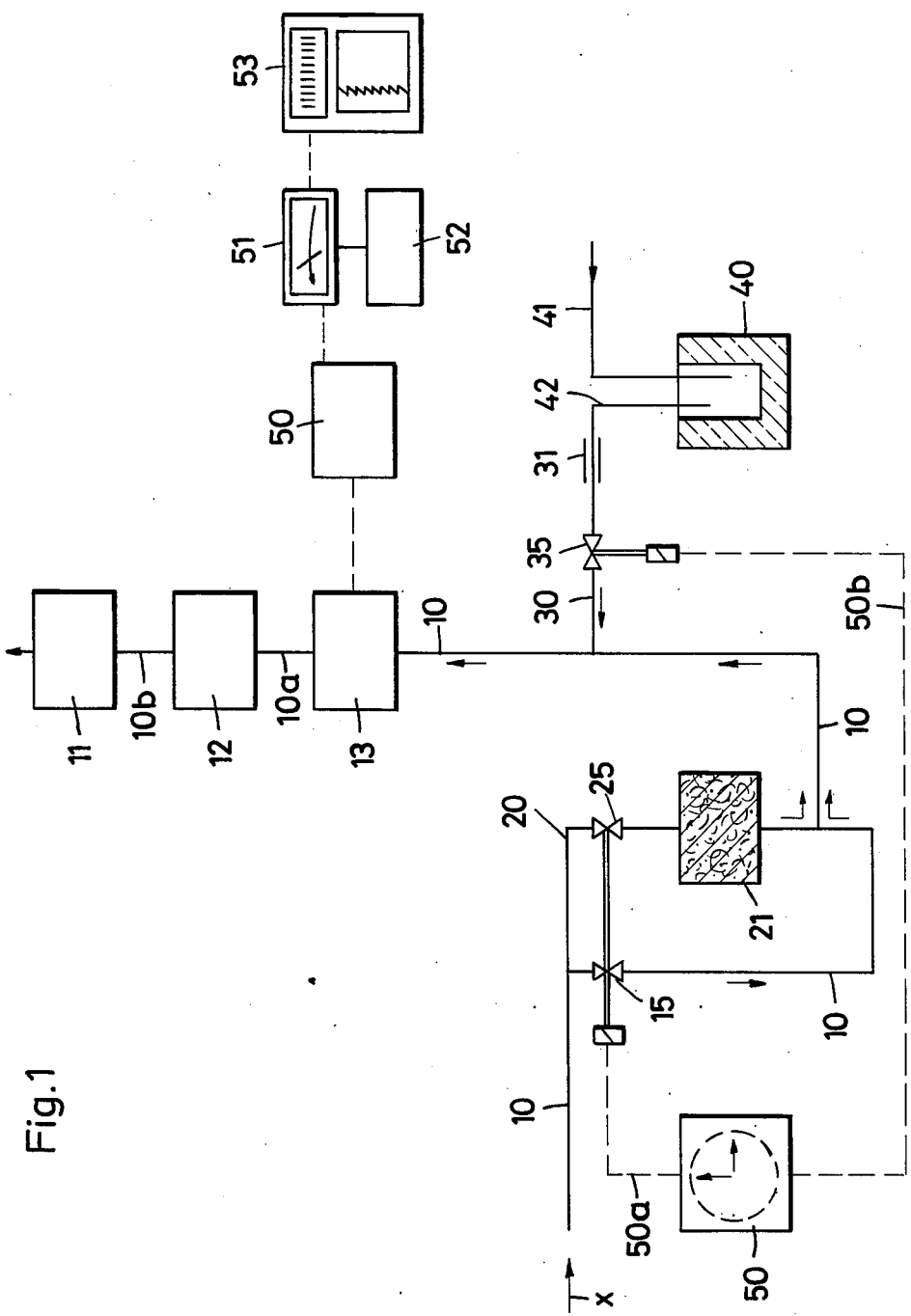

Referring first to FIG. 1, the embodiment of the apparatus for automatically detecting traces of organic solvent vapors in air shown therein will be supplied with a test gas containing the measured component through a feed line 10, as indicated by the arrow X. The feed line 10 is connected to a gas pump such as a diaphragm pump 11. The gas pump 11 draws in the test gas through the feed line 10. To the intake side of the gas pump 11 is connected a flow controller 12, and to the intake side of the flow controller 12 is in turn connected a conventional gas detector which serves as a measuring cell 13. Various types of gas detectors are already known. These gas detectors are permeable for gas so that gases may enter into and exit from the detector. The gas detectors are highly sensitive to the gas that is to be detected. The operation of gas detectors of this type is based on a gas sensitive element which may consist of a metal oxide semiconductor material the electrical conductivity of which varies by adsorption of gas. The gas detector furthermore comprises at least two electrodes which are connected to the gas sensitive element. The gas pump 11 is connected by line 10b to the flow controller 12, and the flow controller 12 is connected by line 10a to the measuring cell 13. The feed line 10 for the test gas includes a control valve 15.

The feed line 10 is connected to a first branch line 20 which is connected to the feed line 10 at points respectively upstream and downstream of the control valve 15. In the branch line 20 is mounted an activated charcoal filter 21 in series with a control valve 25.

At the downstream side of the activated charcoal filter 21 the feed line 10 is connected to a second branch line 30. This second branch line 30 is connected to a calibration unit or receptacle 40 and is connected to the feed line 10 at a point upstream of the measuring cell 13. The calibration unit 40 which will be described in detail further below includes an inlet connection 41 and an an outlet connection 42. The outlet connection 42 is connected to the branch line 30 whereas the inlet connection 41 is adapted to supply test gas or test gas from which the measured component has been eliminated to the calibration unit. In the branch line 30 are connected a control valve 35 and a capillary tube 31 between the junction with the feed line 10 and the calibration unit 40.

The control valves 15, 25 and 35 are preferably solenoid operated valves and are connected by lines 50a and 50b respectively to a conventional program controller 50.

The measuring cell 13 is connected to a voltage supply 50. A display device 51 is connected to the output of the voltage supply 50. An alarm device 52 is coupled to the display device 51. A recorder 53 is connected to the output of the display device 51.

Figure 3:
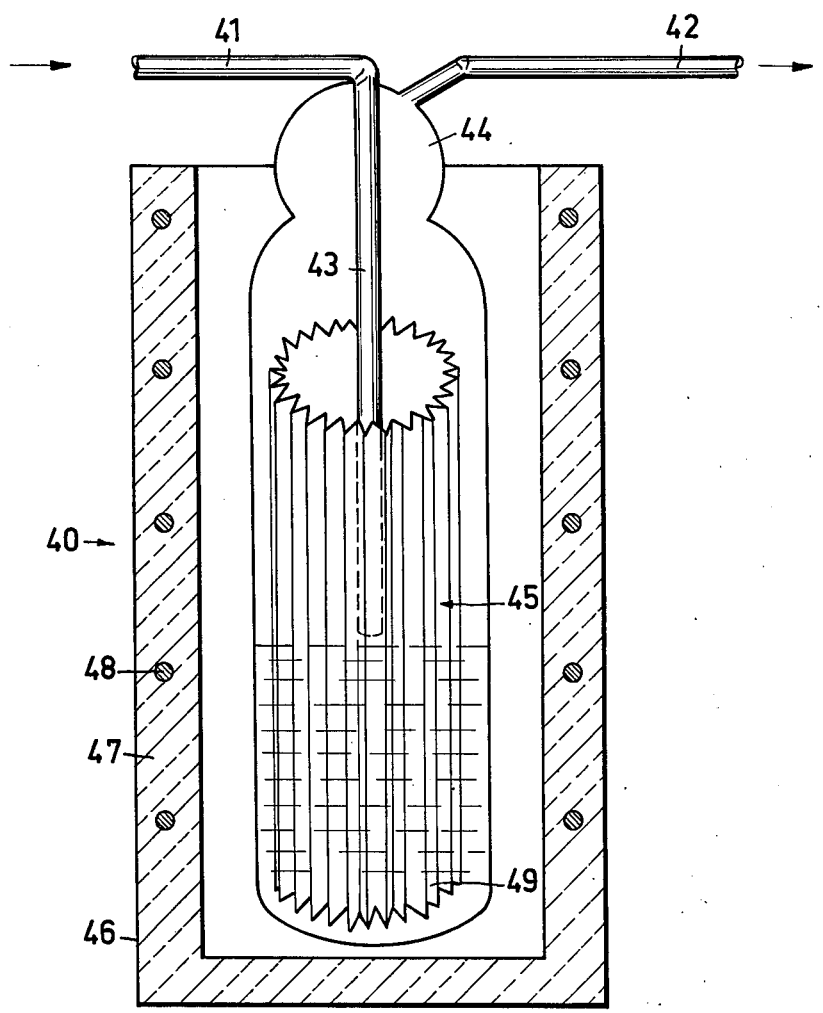
FIG. 3 is a schematical illustration of a calibration unit forming a part of the apparatus for automatically detecting traces of organic solvent vapors in air.

Referring to FIG. 3, there is shown in more detail the calibration unit 40. The calibration unit 40 comprises a washing-bottle type receptacle in which is mounted an inlet line 43 connected to the inlet connection 41. The inlet line 43 extends from the top of the unit downwardly whereby the length of the inlet line 43 is selected so that the free lower end orifice of the inlet line 43 will always be above the level of the fluid contained in the calibration receptacle. At its upper end, the receptacle includes a dome-shaped top header portion 44 into which opens the outlet connection 42. In the interior of the receptacle is provided a large surface evaporator 45 which may comprise at least one filter paper cartridge 49 in which the filter paper is folded in the shape of a cylindrical sleeve of a star-shaped cross-sectional configuration. Instead of a filter paper cartridge 49, several concentrically arranged cylindrical ceramic bodies may be provided. In this connection it is important that the evaporator 45 provides a maximum surface area and consists of a material allowing to evaporate the solvent contained in the receptacle. Test gas from which the measured component has been eliminated will be supplied through the inlet connection 41 into the calibration unit 40. Solvent vapors generated from the solvent contained in the receptacle in combination with test gas from which the measured component has been eliminated will exit from the outlet connection 42 (see FIG. 3).

An essential condition for the automatical detection of traces of organic solvent vapors in air is to monitor in predetermined intervals the zero point and a well defined range value which may be selected at about ¾ of the full measuring range. For the zero point control, there must be supplied air free from the measured gas component. For generating a well defined and constant measuring gas concentration which is suitable for the measuring purpose there may be employed a solvent in fluid phase, provided the gas pressure which will establish above the surface of the fluid in accordance with the Henry Law may be maintained constant over an extended period of time. Toward this end, the invention proposes to employ a calibration unit 40 which is protected against external temperature influences by a corresponding heat insulation and which may be maintained at a constant temperature. The internal space of the calibration unit comprises an unique large surface evaporator 45 the evaporation properties of which are independent of the filling level and the supply of solvent in the receptacle. By modifying the gas streams by means of critically dimensioned nozzles, capillary tubes or measuring diaphragms 31 any desired solvent vapor concentration may be established in test gas such as air from which the measured component has been eliminated or in any other carrier or entraining gas. In the herein proposed calibration unit 40 the solvent to be measured is directly in the liquid phase and not in combination with any additional bonding or diluting agents. The solvent is maintained pressureless within the receptacle of the calibration unit. The vapor pressure that will establish within the calibration receptacle depends preferably on the ambient temperature when idea conditions exist for providing the theoretical vapor pressure. For acetone e.g. 175 torr correspond to about 9.3 Vol. %. Since, however, continuously a well defined amount of gas is withdrawn from the generating receptacle, i.e. from the calibration unit, this loss must be adequately made up by gas generated from the liquid phase.

For comparison purposes, the diffusion rate of prior art calibration devices for the PPB range may be around 100 μg/h whereas the rate discharged from the inventive calibration unit is higher by a factor 1000, i.e. amounts to about 100 mg/h. This greatly increased rate is obtained by means of the large surface evaporator 45 mounted in the calibration unit 40. By using filter paper cartridges 49 which are folded in the shape of a cylindrical sleeve of a star-shaped cross-sectional configuration the filter paper sheets will be constantly wetted by the liquid that is within the receptacle of the calibration unit so that the liquid will diffuse upwardly within the carrier material, i.e. in the filter paper sheets so that a substantially uniform surface humidification is achieved, and this humidification is independent of the filling level and the supply of liquid in the receptacle of the calibration unit.

In the apparatus for automatically detecting traces or organic solvent vapors in air the calibration unit of the present invention operates as follows:

Each of the inlet connection 41 and the outlet connection 42 is restricted by a capillary tube 31 or 38 respectively through which passes the air/gas mixture exiting from the receptacle of the calibration unit or respectively the test gas from which the measured component has been eliminated or carrier gas entering the receptacle. The carrier gas need not be purified, i.e. separated from the measured gas component since the gas concentration generated within the calibration receptacle is about $10^4$ fold higher than ambient air, i.e. carrier gas. By the heat insulation of the outer jacket 46 enclosing the receptacle of the calibration unit 40 and by the additional heating elements 48 within the outer jacket 46 a sufficiently stable thermostatic control may be obtained. The heat insulating material is indicated at 47 in the outer jacket 46 (see FIG. 3).

As may be seen from the schematical illustration of FIG. 1, the program controller 50 serves to establish the zero point control or the calibration operation within predetermined time intervals. The program controller 50 may consist of a switching timer type apparatus. The gas which is intended to be measured, e.g. in room air monitoring, passes through the feed line 10 and through the open solenoid operated control valve 15 and directly into the measuring cell 13. The control valve 25 is closed. From the measuring cell 13 the measured gas passes through the flow controller 12 and to the gas pump 11 which serves to draw in the feed gas through the above mentioned components. The voltage supply 55 serves to electrically stabilize the heating and auxiliary voltages of the gas detector 13 which defines the measuring cell proper. The measuring cell 13 is connected in a bridge circuit which is described further below. The display meter 51 is coupled to an alarm device 52 and to a recorder 53. The devices 51, 52 and 53 are connected to the output of the supply 55.

The zero and calibration controls are initiated several times daily by means of the program controller 50. In this operation, the drawn-in gas sample passes through the open control valve 25 and through the activated charcoal filter 21 in which the measured gas component is retained so that the test gas from which the measured gas component has been eliminated enters into the measuring cell 13. In further steps of the calibration cycle the control valve 35 in the branch line 30 is opened. Since the line leading to the measuring cell 13 is at a negative pressure, a well-defined quantity of solvent vapor will be withdrawn through the capillary tube 31 from the calibration unit 40, and this solvent vapor is admixed with the zero point air. The receptacle of the calibration unit 40 of course contains the solvent which is to be detected in the test gas. The calibration signal generated by the measuring cell 13 will be recorded in the recorder 53.

Upon termination of the calibration operation the program controller 50 resets the apparatus into "measuring" mode, i.e. the control valves 25 and 35 are closed and the control valve 15 is opened. If the indicated calibration value drifts, e.g. because the measuring cell is modified by aging, the alarm device 52 may release an alarm signal for indicating that the measuring cell has changed. The calibration value may likewise be automatically adjusted to a target value.

Figure 2:
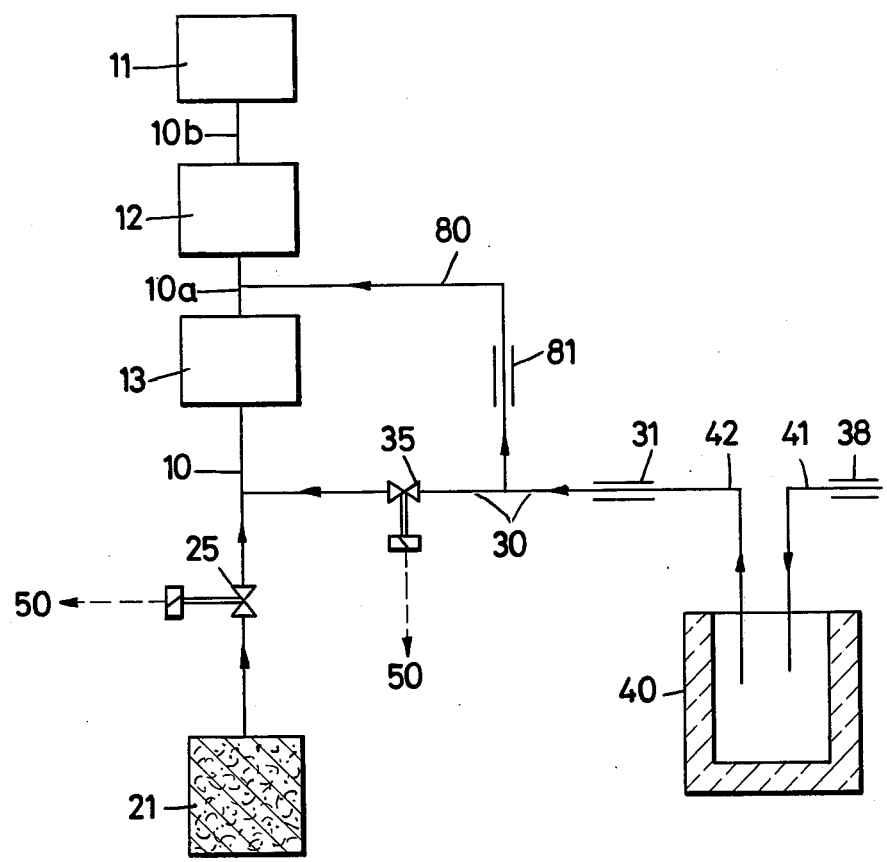
FIG. 2 is a schematical illustration of another embodiment of the apparatus.

Referring to FIG. 2, in this embodiment the branch line 30 is connected through another branch line 80 to the feed line portion 10a between the measuring cell 13 and the flow controller 12, and this branch line 80 is connected to the branch line 30 at a point between the capillary tube 31 and the control valve 35. The branch line 80 mounts an auxiliary capillary tube 81 which allows very fast adjustment of the calibration value when activating the calibration unit. This capillary tube 81 actually represents a bypass for additionally diluting the gas. The inlet connection 41 of the calibration unit 40 may be provided with another capillary tube 38.

The calibration interval may amount to about six hours, and these extended intervals may bring about the effect that solvent vapors within the capillary tube 31 will be adsorbed at the inner walls of the capillary tube so that the concentration is lowered. When opening the control valve 35 for establishing a connection to the carrier gas via the activated charcoal filter 21, considerable time will elapse until the target concentration will be supplied from the receptacle of the calibration unit 40 through the capillary tube 31. The time until the calibration value comes up to the target value may therefore amount up to 30 minutes. By using an auxiliary capillary tube 81 in combination with the other components of the apparatus, the gas or vapor concentration of the calibration receptacle will readily exist at the downstream end of the control valve 35.

The operation of the embodiment shown in FIG. 2 is as follows:

When initiating a calibration cycle, i.e. when employing the calibration unit a well defined quantity of test gas from which the measured gas component has been eliminated and solvent vapor will be withdrawn from the calibration receptacle through the capillary tube 31 by the negative pressure in the system. This test gas/solvent vapor mixture passes through the flow controller 12 and the diaphragm pump 11. The branch line 80 with the auxiliary capillary tube 81 is connected at one end to the branch line 30 upstream of the capillary tube 31 and downstream of the control valve 35, and connected at its other end to the feed line portion 10a upstream of the gas sensor or measuring cell 13 and downstream of the flow controller 12. The capillary tube 81 is suitably dimensioned so that a steady partial gas flow is continuously withdrawn whereby the effective quantity of gas provided through the capillary tube 81 per time unit is reduced when this gas combines with the carrier gas or the test gas from which the measured gas component has been eliminated. Allowance for this reduction is made, however, in the calibration. When closing the control valve 35 for zero control or during the measuring cycle a very small partial flow is continuously discharged from the calibration unit 40 through the capillary tube 31 and the auxiliary capillary tube 81 into the measuring cell 13 and into the feed line portion leading to the diaphragm pump 11.

By this expedient, the measured component does not come to a standstill in the capillary tube 31 during the above mentioned time intervals, i.e. during the measuring cycle, so that the concentration does not alter, e.g. by adsorption effects. When the control valve 35 reopens, the gas concentration required for calibration is immediately available so that the response time for the calibration unit is substantially shortened.

Figure 4:
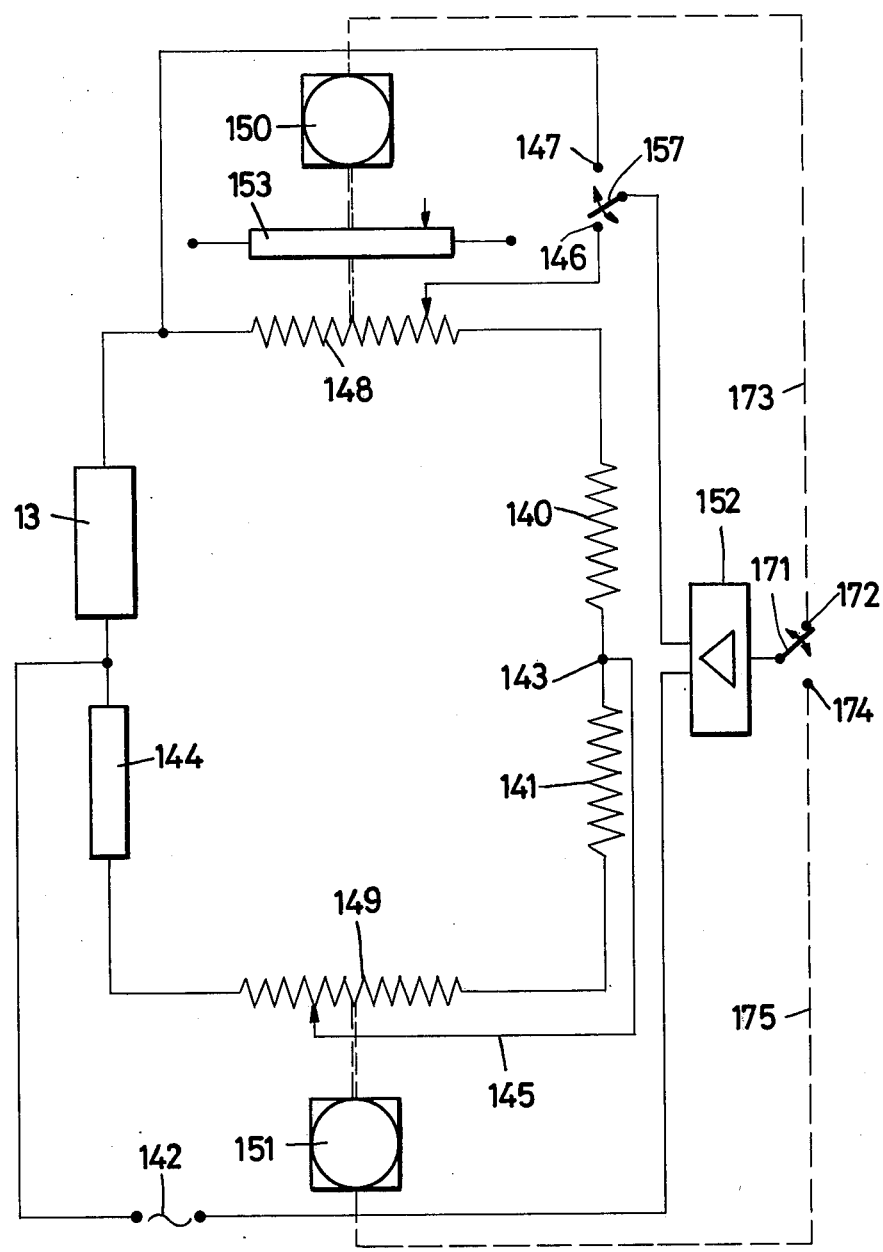
FIGS. 4 and 5 are circuit diagrams of electric measuring systems for the zero compensation of gas traces detector apparatus with integral calibration units.

As pointed out above, the measuring cell 13 is connected in a bridge circuit allowing a zero compensation. This bridge circuit is shown in FIG. 4. A substantial part of this bridge circuit with automatical compensation for zero and measuring values consists of a Wheatstone bridge formed by resistors 140, 141, a measuring potentiometer 148 coupled mechanically to a remote transmitter 153 and a zero potentiometer 149. The measuring potentiometer 148 may be adjusted by means of a servo motor 150, and the zero potentiometer 149 may be adjusted by a second servo motor 151. The bridge supply voltage 142 which may be an a.c. voltage is fed into the circuit at the input junctions 143, 144. Diagonally thereto, at the output terminals 145, 136 and 145, 147 respectively the bridge output voltage is coupled out.

When the measuring cell 13 is supplied with a test gas such as air from which the measured gas component has been eliminated, the measured value is taken as the zero value. The measuring potentiometer 148 is adjusted into its "left-hand end position" by means of an additional potentiometer of the Wheatstone bridge not shown in the drawing. The zero potentiometer 149 will be brought into a substantial midway position. When measuring, the switch arm 157 contacts the output terminal 146 so that the transistorized amplifier 152 is connected to the measuring potentiometer 148 through the line 145, and furthermore to the zero potentiometer 149. When the bridge compensation varies as may be caused e.g. by test gas residues in the measuring cell, the balance adjustment of the bridge circuit varies accordingly. To re-establish the balance of the bridge, the servo motor 150 is operated and adjusts the measuring potentiometer 148 towards the right. The switch arm 171 then engages contact 172 of the line 173 for the servo motor 150.

For the "zero compensation" mode, the switch arm 157 is engaged with the output terminal 147. The transistorized amplifier 152 is then coupled directly to the bridge and the zero potentiometer 149. In this position, the zero positioning of the potentiometer 148, i.e. "left-hand end position" is obtained. The measuring position of the potentiometer 148 is therefore not modified during compensation. The indicated value is recorded in the recorder 53.

For zero changes, e.g. when the measuring cell 13 becomes contaminated, the measuring bridge circuit will be unbalanced when switching over the amplifier input onto "zero" mode by connecting the switch arm 157 to the output terminal 147 of the line 175, in simultaneously passing through the measuring cell 13 test gas from which the measured gas component has been eliminated, i.e. the so-called "zero gas". The servo motor 151 will then adjust the potentiometer 149 until the bridge balance has been reestablished. After reestablishing the bridge balance, the measuring cell 13 is supplied with test gas containing the measured gas component and alternately solvent vapor from the calibration unit 40. The amplifier inputs and outputs are switched over to "measuring" mode by connecting the switch arm 157 to the output terminal 146 and connecting the switch arm 171 to the contact 172.

When the concentration of the measured gas component has not changed in comparison to a previous measurement, the measuring potentiometer 148 does not change its position. If, however, the quantity of measured gas component differs, the potentiometer 148 adjusts to the novel value.

Figure 5:
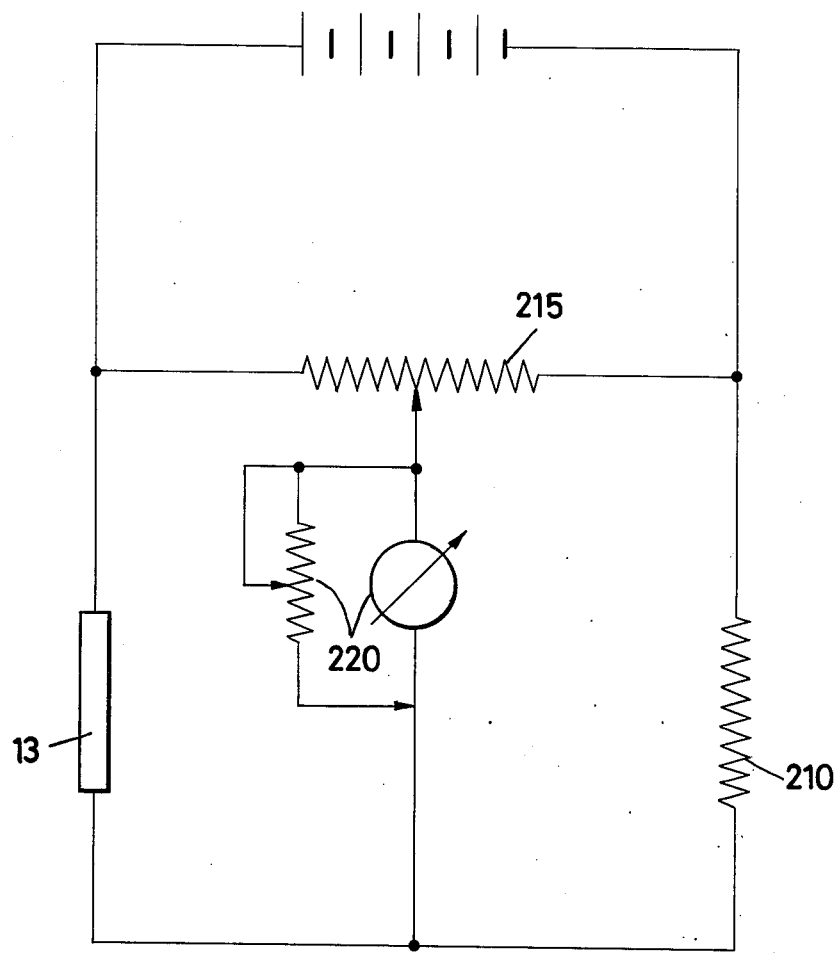

As may be seen in FIG. 5, there may likewise be employed a bridge half circuit with a d.c. supply and manual balance means. In this circuit, the measuring cell is again shown by the reference numeral 13. The reference 210 indicates a reference resistor, and the reference 215 indicates a zero potentiometer. The sensitivity measurement is indicated by 220.

For purposes of practical usage the various components of the apparatus of the present invention may be combined to allow the following arrangements:

1. Usage of the gas detector in combination with suitable electric and electronic stabilizers as a base unit for monitoring filter assmblies e.g. of flue gas purification systems such as adsorbers or chemical reaction scrubbers, or in after-combustion plants wherein exact measurements are of less significance.

2. Combining the base unit with the calibration unit and performing automatic controls of the zero point and of the calibration value for highly precise monitoring of maximum admissible working place concentrations, as well as for recording monitored values.

3. The calibration unit with large surface evaporator in combination with suitable capillary systems and a zero point gas supply may be used for controlling and calibrating test gas tubes.

Figure 6:
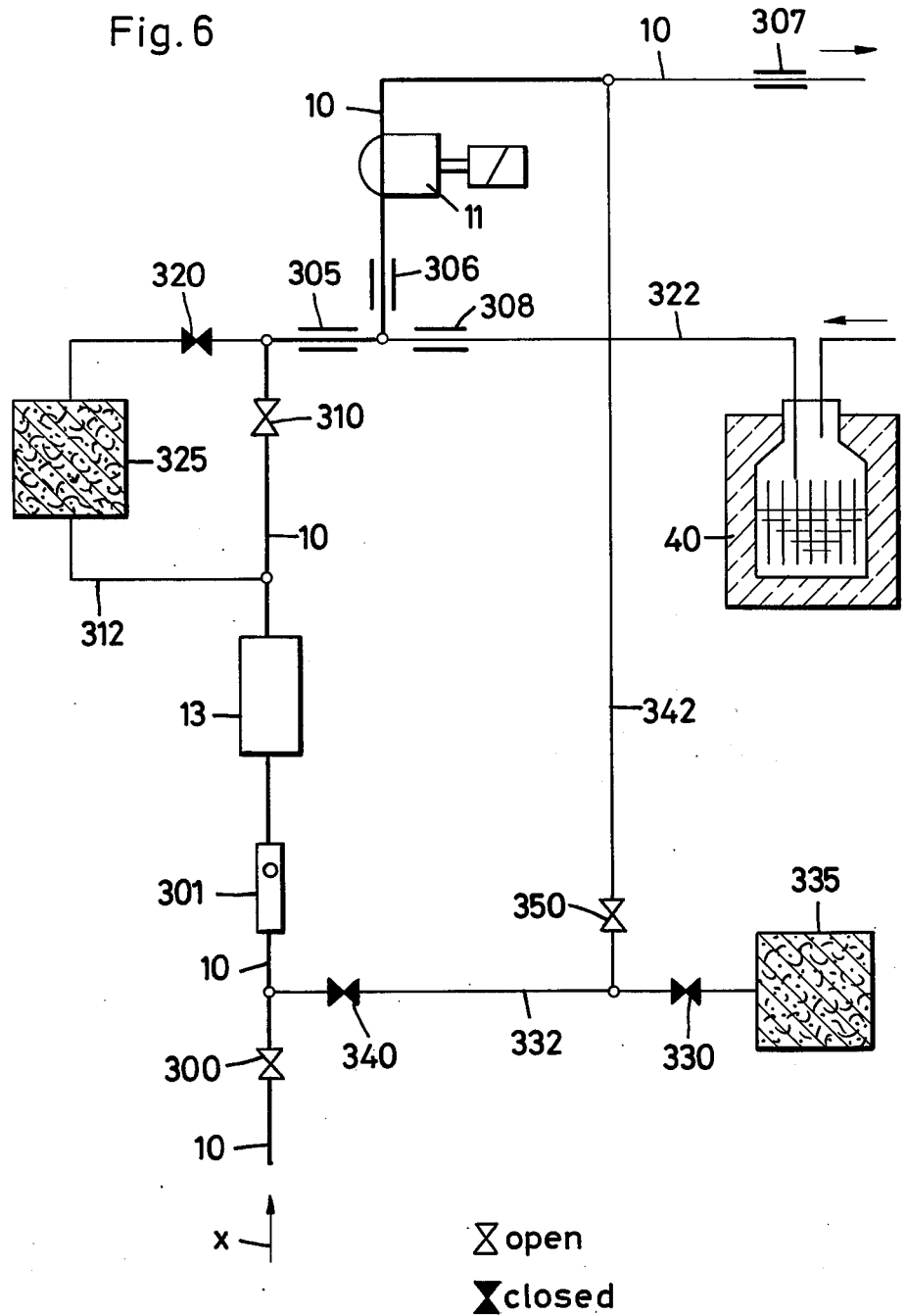
FIG. 6 is a schematical illustration of an apparatus in the "measuring" mode.
Figure 7:
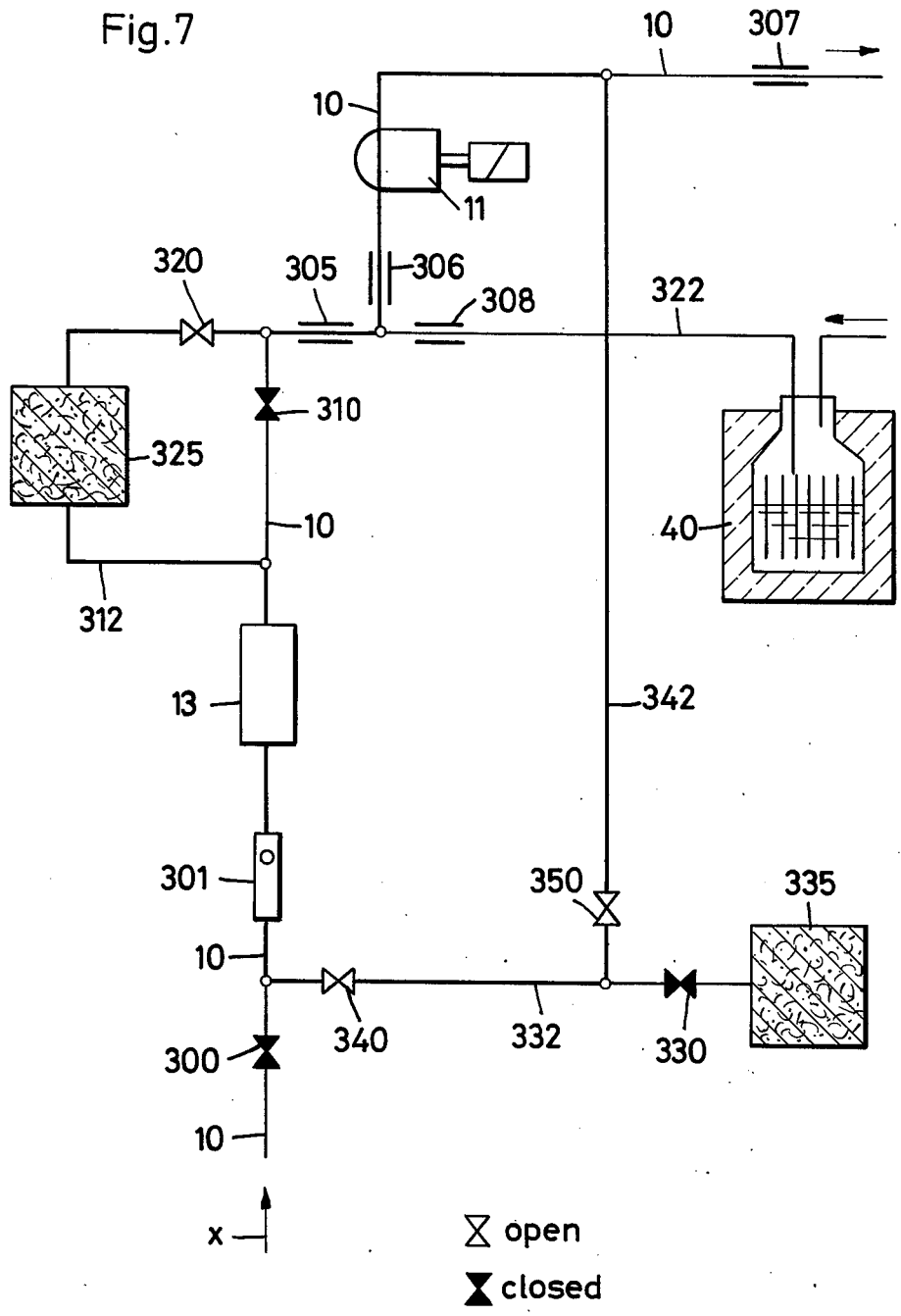
FIG. 7 is an illustration of the apparatus of FIG. 6 in the "calibration" mode.
Figure 8:
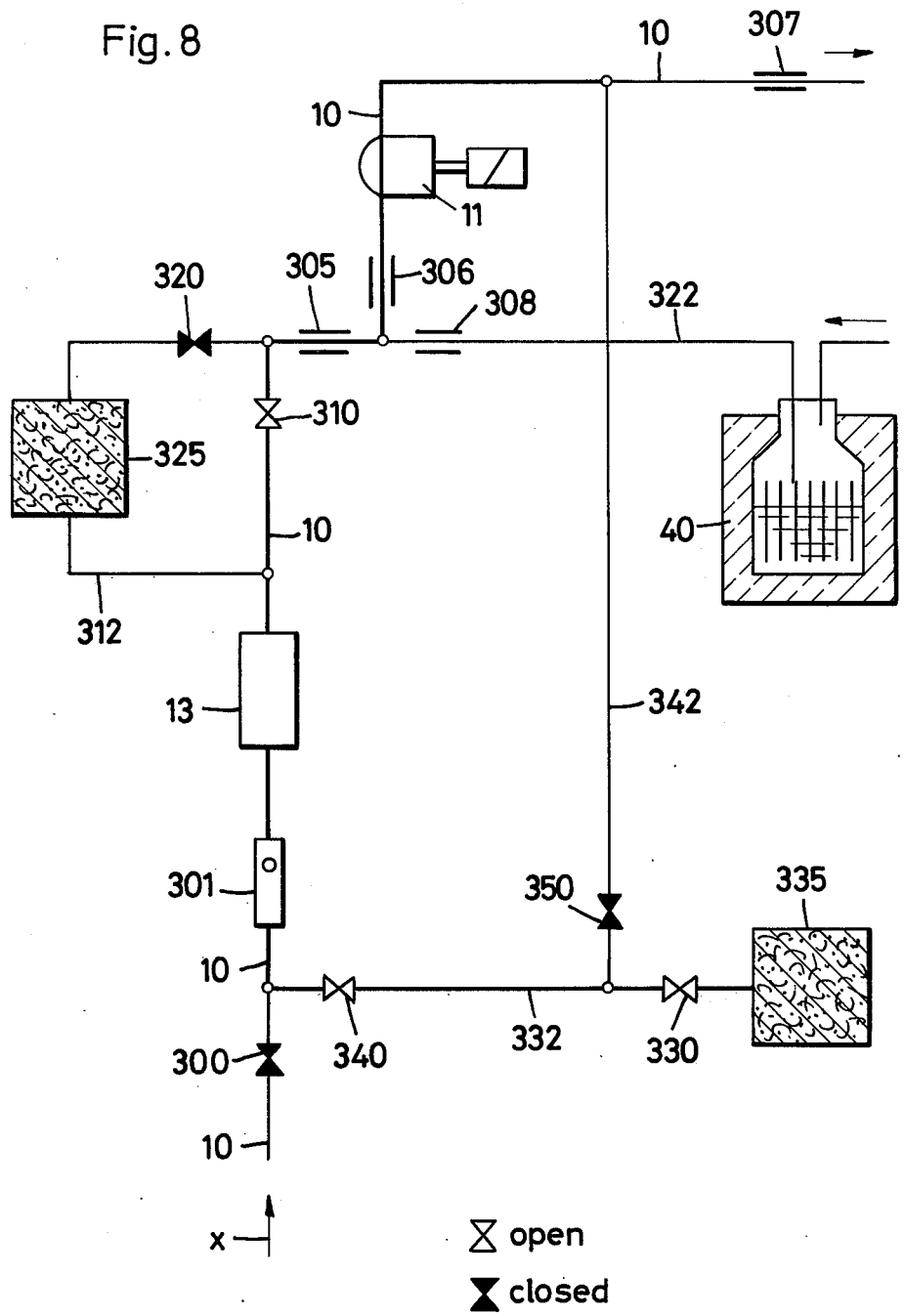
FIG. 8 is an illustration of the apparatus of FIG. 6 in the "zero" mode.

In the embodiment of the inventive apparatus shown in FIGS. 6 to 8 the feed line 10 is provided with a shutoff valve 300 connected at its upstream side to a rotameter 301. To the output of the rotameter 301 is connected a measuring cell 13, and to the output of the measuring cell 13 is connected another shutoff valve 310. The upstream side of the shutoff valve 310 is connected through two capillary tubes 305 and 306 to the input side of the gas pump 11. At the output of the gas pump 11 is provided another capillary tube 307 in the feed line 10.

A branch line 312 is connected in parallel to the feed line 10 and connected to the latter at a point between the measuring cell 13 and the shutoff valve 310 and respectively to a point between the shutoff valve 310 and the capillary tube 305. The branch line 312 includes an activated charcoal filter 325 and another shutoff valve 320 connected to the output side of the filter 325.

The feed line 10 is connected through a further branch line 322 to the calibration unit 40. The branch line 322 is connected to the feed line 10 between the two capillary tubes 305 and 306. In the branch line 322 is mounted another capillary tube 308.

The feed line 10 is furthermore connected to another branch line 322 with another charcoal filter 335. This branch line 332 is connected to the feed line 10 between the shutoff valve 300 and the rotameter 301. The branch line 332 mounts two shutoff valves 330 and 340.

The branch line 332 is connected through a further branch line 342 with a shutoff valve 350 to the feed line 10. The branch line 342 is connected at a point between the two shutoff valves 330, 340 to the branch line 332, and at its other end between the diaphragm pump 11 and the capillary tube 307 to the feed line 10.

The shutoff valves 300, 310, 320, 330, 340 and 350 shown in the measuring apparatus of FIGS. 6 to 8 may be combined two by two into three-way valves so that the two shutoff valves 310, 320, the two shutoff valves 300, 340 and the two shutoff valves 330, 350 define each a three-way valve assembly.

The operation of the embodiment shown in FIGS. 6 to 8 will be described in the following whereby FIG. 6 shows the "measuring" mode, FIG. 7 shows the "calibration" mode and FIG. 8 shows the "zero point" or "zero" mode. In these FIGS., the active gas circuit in each operational mode is shown by the thicker black connections.

In the "measuring" mode the gas circuit is as shown in FIG. 6: The gas pump 11 draws in test gas containing the measured component through the feed line 10. The test gas passes through the rotameter 301 and through the capillaries 306, 307 to the gas pump 11 and is discharged therefrom through the capillary 307 to the outlet of the feed line 10. The capillary tube 307 serves for pressure relief and pressure balance in the circuit or to vent the test gas when the shutoff valve 350 is closed, as may be seen from FIGS. 2 and 3. The shutoff valves are then actuated as follows: The shutoff valves 320, 330 and 340 are closed, and the shutoff valves 300, 310, 350 are open.

The capillary tube 308 serves to supply a well defined test gas stream from the calibration unit 40. The carrier gas rate through the calibration unit 40 is maintained constant by the restricting capillary tube 306 and the gas pump 11. During measurement, solvent vapor is continuously withdrawn from the calibration unit 40 whereby this solvent vapor is added upstream of the measuring cell 13 and thus does not interfere with the measurements.

In the operational mode "calibration" as shown in FIG. 7 the gas cycle is as follows: The test gas input is blocked by the shutoff valve 300. The gas pump 11 draws in the carrier gas stream through the capillary tubes 305 and 306, the open shutoff valve 320 (the shutoff valve 310 being closed), the activated charcoal filter 325, the measuring cell 13 and the rotameter 301. From the discharge side of the gas pump 11 the calibration gas mixture is discharged through the open valves 350 and 340 and through the rotameter 301 into the measuring cell 13 in thus completing the closed cycle. The gas exiting from the measuring cell 13 is freed from the measured gas component in the activated charcoal filter 325 so that the carrier gas, i.e. air passing through the capillary system 305, 306, 308 is of an originally predetermined well defined gas concentration. This gas is supplied to the measuring cell 13 along the above described closed circuit path. In the operational mode "calibration" the capillary tube 307 serves as a pressure relief. During the "calibration" mode, the shutoff valves 300, 310, 330 are closed and the shutoff valves 320, 340 and 350 are open.

The described arrangement has the advantage that the calibration gas stream which is permanently generated during the operational mode "measuring" is immediately available when switching over to "calibration" so that adjustment of the calibration value may be effected quite rapidly.

For avoiding any unnecessary loading of the activated charcoal filter 325 during the measuring mode which amounts to a multiple of the time allotted for calibration, the gas stream exiting from the measuring cell 13 is introduced directly through the open shutoff valve 310 into the capillary system 305, 306, 308.

In the operational mode "zero control" the gas flow is as shown in FIG. 8: The zero point circuit is similar to the measuring circuit insofar as the gas exiting from the measuring cell 13 is passing through the open valve 310, through the capillary system 305, 306, 308, through the gas pump 11 and through the capillary tube 307 to the vent opening. The zero point gas is obtained by supplying the measuring cell 13 with gas passed through the activated charcoal filter 335 whereby the shutoff valves 330 and 340 are open. In the operational mode shown in FIG. 8 the shutoff valves 300, 320 and 350 are closed, whereas the shutoff valves 310, 330 and 340 are open.

The technical advantages of the measuring system reside in the closed circuit recycling of the calibration gas and the fast response characteristics of the measuring cell which continuously provide a well defined calibration gas concentration.

Figure 9:
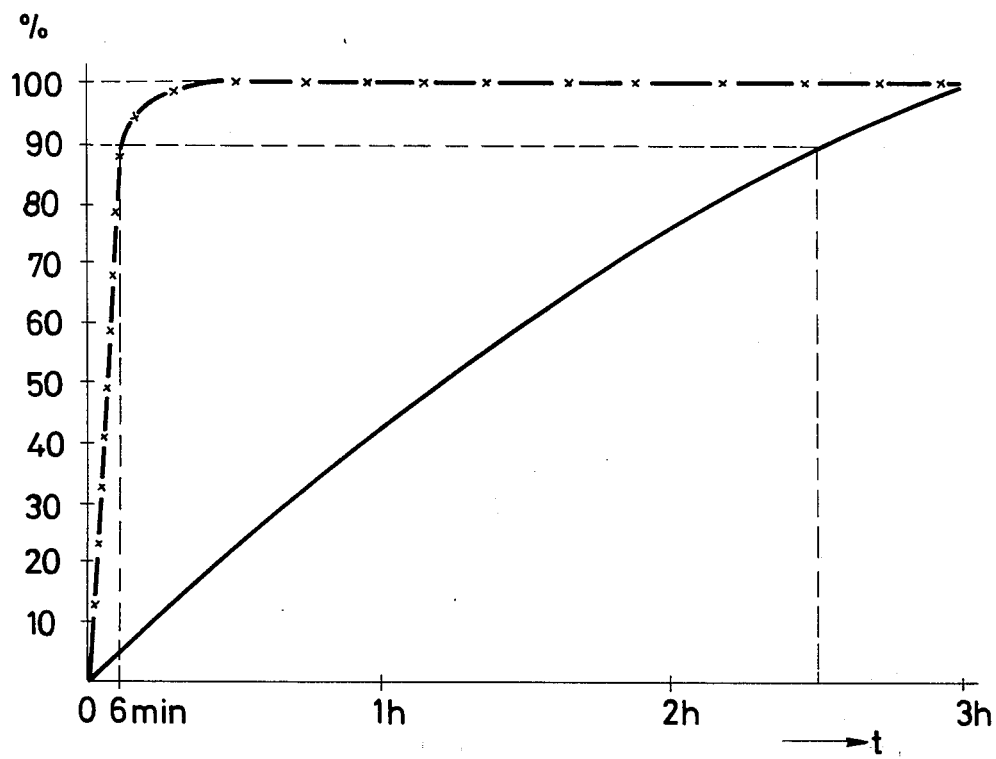
FIG. 9 is a diagram for explaining the operation of the apparatus.

The diagram of FIG. 9 illustrates the efficiency of the closed circuit system, i.e. the faster response characteristic of the calibration gas as compared to prior art apparatus. FIG. 9 depicts the calibration gas concentration versus time in a prior art measuring apparatus (continuous curve) and for an apparatus in accordance with the present invention (broken curve). The dashed or broken line curve shown in the diagram illustrates clearly that the calibration cycles may be substantially shorter in thus increasing considerably the availability of the detecting apparatus for measuring cycles. Whereas in the prior art detecting systems the 90 percent level will not be established until after about 2 hours or longer, this level may be obtained within a few minutes only in the system of the present invention.

The embodiments of the invention in which an exclusive property or privilege is claimed are defined as follows:

1. Apparatus for the automatic determination of traces of organic solvent vapors in air, using a nonspecific gas detector, particularly a gas semiconductor as a measuring cell, by comparative measurements of the test gas containing the measuring components with a reference gas containing the measuring component, comprising a feed line for test gas, the feed line connected with a gas pump to which is attached a flow controller, a gas detector functioning as a measuring cell including a control valve, a first branch pipe opening below the latter into the feed line, the first branch pipe including an activated charcoal filter with attached control valve, a second branch pipe between the active charcoal filter and the measuring cell, said second branch pipe connected with an outlet connection of a calibration unit which has a control valve ahead of the calibration unit and a capillary tube arranged between the latter and the calibration unit, the control valves being designed as magnetic valves and connected to a program switch mechanism, said calibration unit comprising a heat-insulated, washbottle-type container with a feed pipe for the test gas liberated of the measuring component, which terminates with its free end above the level of the liquid in the calibrating container, and with a discharge pipe arranged in the upper dome of the container, for discharging the solvent vapor concentration from the calibration unit and a large surface evaporator arranged in the interior of the container, which is formed at least of one star-shaped cuff of filter paper and of severally concentrically arranged cylindrical ceramic bodies.

2. An apparatus according to claim 1, wherein a control valve is connected in the feed line, said first branch pipe is connected to the feed line at two points respectively located downstream and upstream of said control valve, said second branch pipe is connected to the feed line at a point upstream of said activated charcoal filter and downstream of said measuring cell, the measuring cell is connected to a measuring system, the measuring system including a fixed resistor and a pair of resistors, said pair of resistors being connected in a Wheatstone bridge circuit including a measuring potentiometer coupled to a first servo motor, and including a zero potentiometer coupled to a second servo motor.

3. Apparatus for the automatic determination of traces of organic solvent vapors in air, using a non-specific gas detector, particularly a gas semiconductor as a measuring cell, by comparative measurements of the test gas containing the measuring component with a reference gas containing the measuring component, comprising a feed line for test gas, the feed line connected with a gas pump to which is attached a flow controller, a gas detector functioning as a measuring cell including a control valve, a first branch pipe opening below the latter into the feed line, the first branch pipe including an activated charcoal filter with attached control valve, a second branch pipe between the active charcoal filter and the measuring cell, said second branch pipe connected with an outlet connection of a calibration unit which has a control valve ahead of the calibration unit and a capillary tube arranged between the latter and the calibration unit, the control valves being designed as magnetic valves and connected to a program switch mechanism, said calibration unit comprising a heat-insulated, washbottle-type container with a feed pipe for the test gas liberated of the measuring component, which terminates with its free end above the level of the liquid in the calibrating container, and with a discharge pipe arranged in the upper dome of the container, for discharging the solvent vapor concentration from the calibration unit and a large surface evaporator arranged in the interior of the container, which is formed at least of one star-shaped cuff of filter paper and of several concentrically arranged cylindrical ceramic bodies, said apparatus for maintaining the gas of vapor concentration in the calibration unit, a third branch pipe being connected at one end to said second branch pipe at a point upstream of said capillary tube in said second branch pipe connected to said calibration unit, the other end of said third branch line connected to said feed line at a point intermediate said measuring cell and said flow controller, said third branch line including an auxiliary capillary tube.

4. An apparatus according to claim 3, wherein said calibration unit container is enclosed in an outer jacket of a heat insulating material provided with heating means.

5. An apparatus according to claim 3, wherein said measuring cell is connected to a d.c. circuitry with manual adjustment means.

* * * * *